United States Patent [19]

Glassman et al.

[11] Patent Number: 5,086,401
[45] Date of Patent: Feb. 4, 1992

[54] IMAGE-DIRECTED ROBOTIC SYSTEM FOR PRECISE ROBOTIC SURGERY INCLUDING REDUNDANT CONSISTENCY CHECKING

[75] Inventors: Edward Glassman, New York, N.Y.; William A. Hanson, Mountain View, Calif.; Peter Kazanzides, Davis, Calif.; Brent D. Mittelstadt, Placerville, Calif.; Bela L. Musits, Hopewell Junction, N.Y.; Howard A. Paul, Loomis, Calif.; Russell H. Taylor, Ossining, N.Y.

[73] Assignee: International Business Machines Corporation, Armonk, N.Y.

[21] Appl. No.: 523,611

[22] Filed: May 11, 1990

[51] Int. Cl.$^5$ .............................. A61B 17/56
[52] U.S. Cl. .................. 395/94; 364/413.01; 364/413.13; 606/53; 606/88; 395/93; 395/95; 395/96; 395/89
[58] Field of Search .................. 364/513; 606/53; 128/25 R, 653 R, 363 B; 378/164; 318/563

[56] References Cited

U.S. PATENT DOCUMENTS

| | | | |
|---|---|---|---|
| 4,150,326 | 4/1979 | Engelberger et al. | 318/563 |
| 4,485,453 | 11/1984 | Taylor . | |
| 4,618,978 | 10/1986 | Cosman | 378/164 |
| 4,691,694 | 9/1987 | Boyd et al. | 128/25 R |
| 4,750,487 | 6/1988 | Zanetti | 128/303 B |
| 4,791,934 | 12/1988 | Brunnett . | |
| 4,945,914 | 8/1990 | Allen | 128/653 R |
| 4,979,949 | 12/1990 | Matsen, III et al. | 606/53 |
| 4,991,579 | 2/1991 | Allen | 128/653 R |

FOREIGN PATENT DOCUMENTS

| | | |
|---|---|---|
| 114505 | 8/1984 | European Pat. Off. . |
| 0326768 | 8/1989 | European Pat. Off. . |
| 3447365 | 12/1984 | Fed. Rep. of Germany . |
| 59-157715 | 9/1984 | Japan . |
| 60-231208 | 11/1985 | Japan . |
| 2094590 | 9/1982 | United Kingdom . |

OTHER PUBLICATIONS

"Computer Assisted Surgery", IEEE Computer Graphics and Applications, vol. 1, No. 3, May 1990 (IEEE).

Kaiura, *Robot-Assisted Total Knee Arthroplasty—Investigation of the Feasibility and Accuracy of the Robotic Process*, Master's Thesis, V. Washington, 1986.

Arai et al., "Bilateral Control for Manipulators with Different Configurations", *IFCON '84*, pp. 40–45.

"Robotic Instrumentation in Total Knee Arthroplasty", by J. L. Garbini et al., 33rd Annual Meeting, Orthopaedic Research Society, Jan. 1987, California, p. 413.

(List continued on next page.)

Primary Examiner—Michael R. Fleming
Assistant Examiner—Roger S. Joyner
Attorney, Agent, or Firm—Perman & Green

[57] ABSTRACT

A robotic surgical system (10) includes a multiple degree of freedom manipulator arm (14) having a surgical tool (22). The arm is coupled to a controller (24) for controllably positioning the surgical tool within a three dimensional coordinate system. The system further includes a safety monitoring processor (38) for determining the position of the surgical tool in the three dimensional coordinate system relative to a volumetric model. The volumetric model may be represented as a constructive solid geometry (CSG) tree data structure. The system further includes an optical tracking camera system (28, 32) disposed for imaging a region of space that includes at least a portion of the manipulator arm. An output of the camera system is coupled to the processor (38) that processes the volumetric model for determining if the surgical tool is positioned outside of the volumetric model. The system further includes a strain gage (40) for detecting slippage in three dimensions between an immobilized tissue, such as bone, and a reference point (44). The system also includes multiple and redundant safety features for suspending a motion of the surgical tool to prevent the tool from operating outside of the predetermined volume of space.

23 Claims, 4 Drawing Sheets

OTHER PUBLICATIONS

"Watchdog Safety Computer Design and Implementation", by R. D. Kilmer, H. G. McCain, M. Juberts and S. A. Legowik, RI/SME Robots 8 Conference, Jun. 1984, pp. 101-117.

"An Articulated Neurosurgical Navigation System Using MRI and CT Images", by Y. Kosugi et al., IEEE Transactions on Biomedical Engineering, vol. 35, No. 2, Feb. 1988.

"A Robot with Improved Absolute Positioning Accuracy for CT Guided Stereotactic Brain Surgery", by Y. Kwoh et al., IEEE Transactions on Biomedical Engineering, vol. 35, No. 2, Feb. 1988.

School of Medicine, University of California, *UC Davis Medical Background,* Feb. 11, 1988.

IBM, University of California Developing Robot-Assisted Surgical Procedure, Feb. 11, 1988.

"IBM Robotics Technology Background", Feb. 11, 1988.

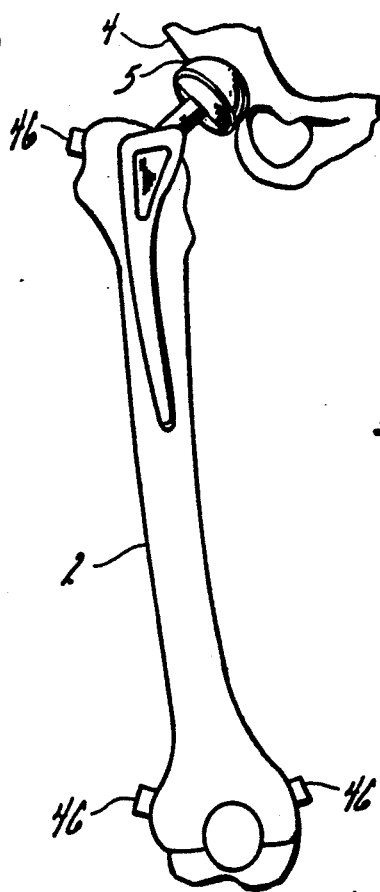
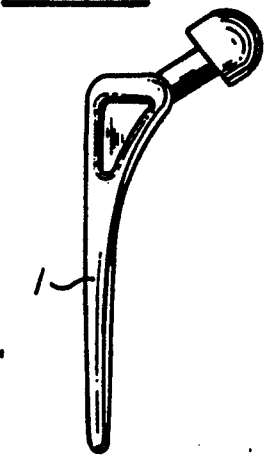
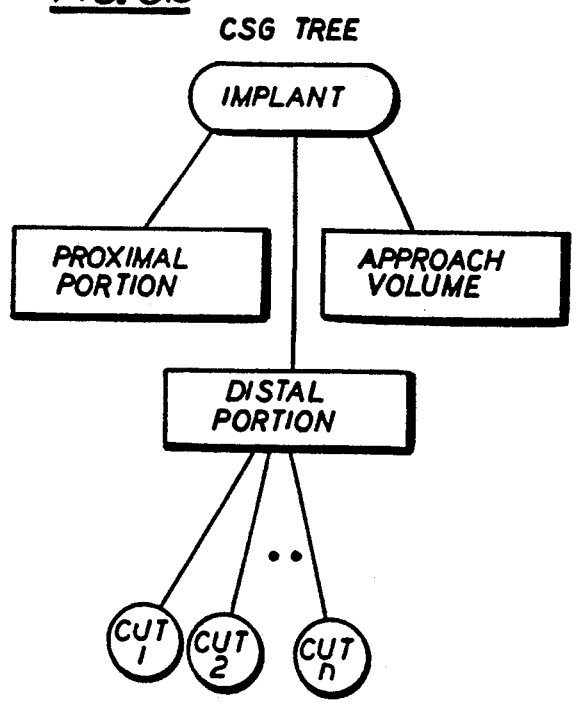
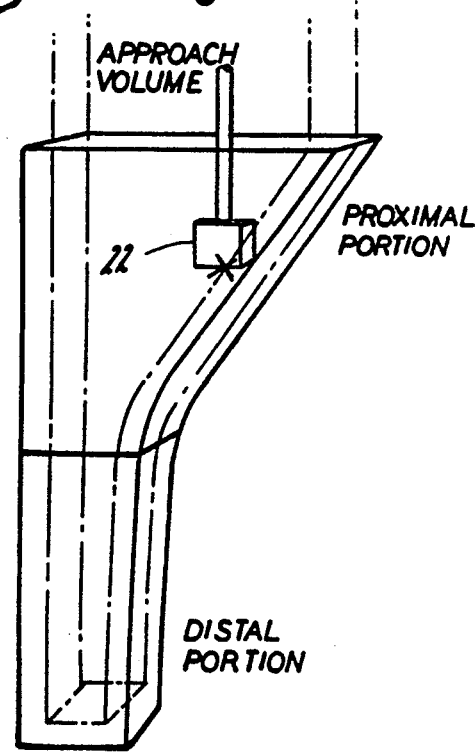

PRE-SURGICAL
PLANNING
INFORMATION
FLOW

IMAGE-DIRECTED ROBOTIC SYSTEM FOR PRECISE ROBOTIC SURGERY INCLUDING REDUNDANT CONSISTENCY CHECKING

FIELD OF THE INVENTION:

This invention relates generally to robotic systems and, in particular, to a robotic system that integrates an interactive Computed Tomography (CT)-based presurgical planning component with a surgical system that includes a multiple-degree of freedom robot and redundant motion monitoring. An illustrative application is presented in the context of a system that prepares a femoral cavity to have a shape precisely determined for receiving a cementless prosthetic hip implant

BACKGROUND OF THE INVENTION:

It has been found that computed tomography (CT) imaging and computer modelling methods provide a precision for pre-surgical planning, simulation, and custom implant design that greatly exceeds the precision of subsequent surgical execution. For example, approximately one half of the 300,000 total hip replacement operations performed each year use cementless implants. Stability of the implant, uniform stress transfer from the implant to the bone, and restoration of the proper biomechanics critically affect efficacy and, in turn, are significantly affected by the proper placement of the implant relative to the bone. An important factor in achieving proper placement of the implant is the accuracy with which the femoral cavity is prepared to match the implant shape.

Recently reported research confirms that gaps between implant and bone significantly affect bone ingrowth. One study of the standard manual broaching method for preparing the femoral cavity found that the gaps between the implant and the bone is commonly in the range of one millimeter to four millimeters and that the overall resulting hole size was 36% larger than the broach used to form the hole. As a result, only 18-20 percent of the implant actually touches bone when it is inserted into such a hole. Furthermore, the placement of the implant cavity in the bone, which affects restoration of biomechanics, is as much a function where the broach "seats" itself as of any active placement decision on the part of the surgeon.

Typically, precise surgical execution has been limited to procedures, such as brain biopsies, for which a suitable stereotactic frame is available. However, the inconvenience and restricted applicability of these devices has led some researchers to explore the use of robots to augment a surgeon's ability to perform geometrically precise tasks planned from CT or other image data.

Safety is an obvious consideration whenever a moving device such as a robot is used in the vicinity of a patient. In some applications, the robot does not need to move during the "in-contact" part of the procedure. In these applications the robot moves a passive tool guide or holder to a desired position and orientation relative to the patient. Brakes are then set and motor power is turned off while a surgeon provides whatever motive force is needed for the surgical instruments. Other surgical applications rely on instrumented passive devices to provide feedback to the surgeon on where the instrument is located relative to an image-based surgical plan.

In an IBM Research Report (RC 14504 (#64956) 3/28/89) R. H. Taylor et al. describe a robotic system for milling a correctly shaped hole into a femur for receiving a cementless hip implant. The system computes a transformation between CT-based bone coordinate data and robot cutter coordinates. The transformation is accomplished in part by a combination of guiding and tactile search used to locate a top center of each of three alignment pins that are pre-surgically affixed to the femur and CT-imaged. This robotic system includes a vision subsystem to provide a redundant check of the robot's motion to ensure that the tool path does not stray outside of a planned work volume. An online display is provided for the surgeon to monitor the progress of the operation. Proximity sensors may be positioned to detect any subsequent motion of the pins relative to a robot base.

SUMMARY OF THE INVENTION

The invention discloses a robotic surgical system that includes a multiple degree of freedom manipulator arm having a surgical tool. The arm is coupled to a controller for controllably positioning the surgical tool within a three dimensional coordinate system. The system further includes apparatus for determining the position of the surgical tool in the three dimensional coordinate system relative to a volumetric model. The determining apparatus includes a device for detecting a location of the surgical tool, such as an optical tracking system disposed for imaging a region of space that includes at least a part of the manipulator arm. An output of the tracking system is coupled to a processor that processes the volumetric model for determining if the surgical tool is positioned outside of a predetermined volume of space. The system further includes redundant safety checks including a strain gage for detecting in three dimensions any slippage between an immobilized tissue, such as bone, and a reference point and also a force sensor coupled to the surgical tool The multiple and redundant safety devices are employed for suspending a motion of the surgical tool to prevent the tool from operating outside of the volumetric model. The coordinates and structure of the volumetric model are determined during a pre-surgical planning session wherein a surgeon interactively selects and positions a suitably shaped implant relative to images of the bone within which the implant is to be installed.

BRIEF DESCRIPTION OF THE DRAWING

The above set forth and other features of the invention are made more apparent in the ensuing Detailed Description of the Invention when read in conjunction with the attached Drawing, wherein:

FIG. 2a illustrates a human hip prosthetic implant;

FIG. 2b illustrates the implant of FIG. 2a implanted within a femur, the Figure also showing the placement of three alignment pins upon the femur;

FIG. 3a illustrates a method of determining a cutter work volume for the implant of FIG. 2a;

FIG. 3b is a CSG tree representation of the cutter work volume of FIG. 3a;

DETAILED DESCRIPTION OF THE INVENTION

Figure 1:
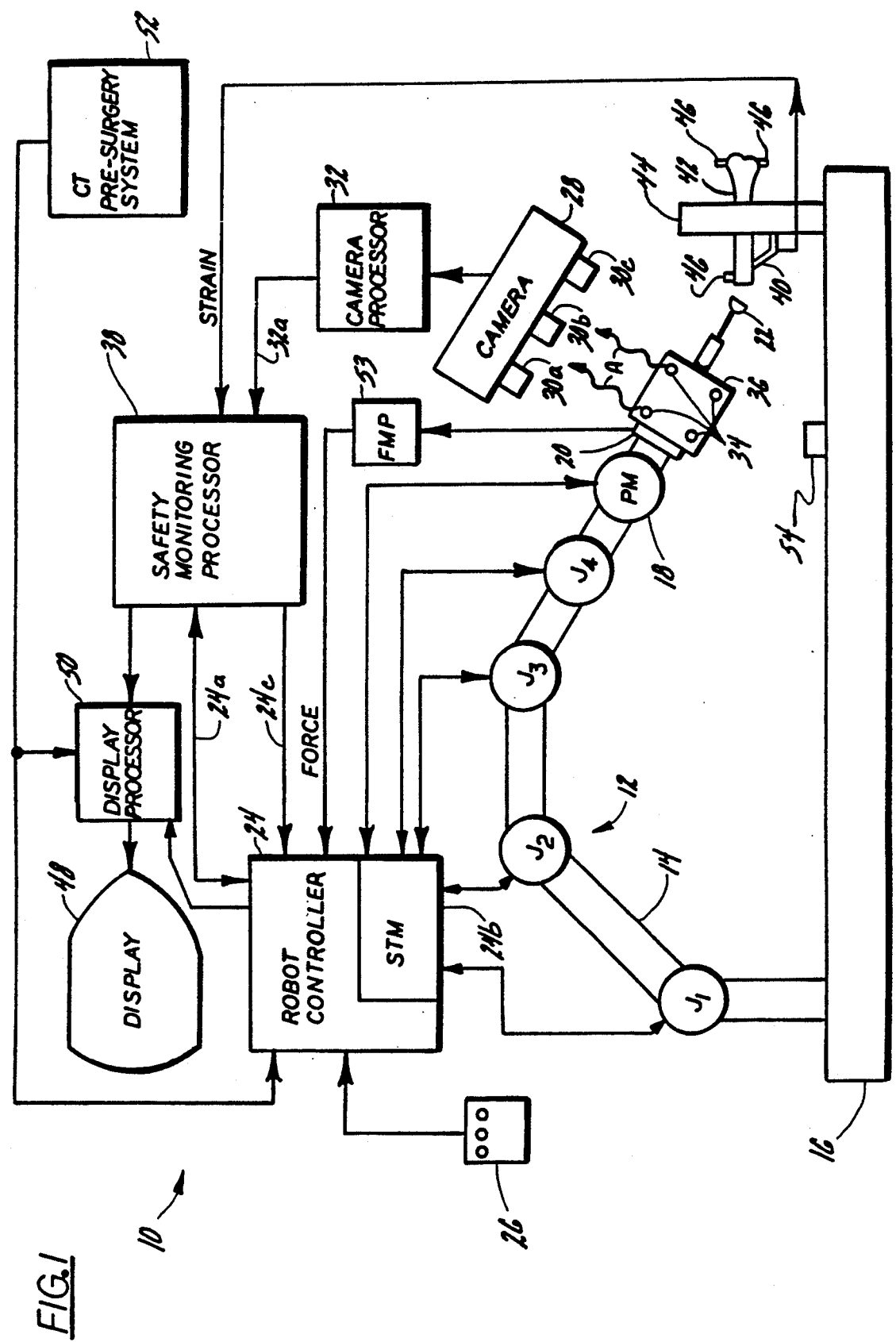
FIG. 1 is a block diagram showing a presently preferred embodiment of a surgical robotic system.

FIG. 1 is a block diagram illustrating a present embodiment of a surgical robotic system 10. System 10 includes a robot 12 having a manipulator arm 14 and a base 16. The arm 14 has at least 5-axes of motion and includes a plurality of joint (J) motors J1, J2, J3 and J4 that provide four degrees of motion and, in the present embodiment, a pitch motor (PM) 18 that provides the fifth degree of motion. In the present embodiment of the invention the robot 12 is a four-degree of freedom IBM 7575 or 7576 SCARA manipulator having an additional pitch axis (IBM is a registered trademark of the International Business Machines Corporation). The PM 18 is presently implemented with a stepper motor having an encoder, primarily for stall detection, that is controlled with a commercially available indexer of the type that accepts a user provided acceleration, velocity and distance commands. Each of the manipulator arm joints has an associated controlling microprocessor.

The robot 12 further includes a six degree-of-freedom wrist-mounted force sensor 20. One suitable force sensor is known as a Lord Force/Torque Wrist Sensor, Model F/T-30/100 having a maximum force limit of 30 pounds and a resolution of 1/40 pound. The force sensor 20 is coupled via a serial or a parallel interface to a robot controller 24.

The robot 12 further includes an end effector having a cylindrical high-speed (65000 rpm) pneumatic surgical cutting tool 22. During surgery all but the robot's end-effector are covered by a sterile sleeve, the end-effector being separately sterilized. The robot 12 is positioned relative to an operating table such that it has ready access to the surgical region.

The robot controller 24 provides servocontrol, low-level monitoring, sensor interfaces, and higher-level application functions implemented in the AML/2 language. The controller 24 is presently embodied in an industrial IBM Personal Computer AT data processor wherein low-level servo control and force sensor interface is provided by suitable printed circuit cards that are plugged into the processor bus (Personal Computer AT is a registered trademark of the International Business Machines Corporation). Controller 24 includes an AML/2 Language Interpreter and also Motion Control System (MCS) software. A commercial version of this software is described in "AML-2 Language Reference Manual", Manual #G7X1369 and in "AML-2 Manufacturing Control System User's Guide", Manual #G67X1370, both of which are available from IBM Manufacturing Systems Products, Boca Raton, Florida.

In the present embodiment the AML/2 software is modified to accommodate the operation of the PM 18 and the force sensor 20. During surgery, the force sensor 20 is employed in conjunction with a Force Monitoring Processor (FMP) 53 to support redundant safety checking, tactile searching to locate aligning pins, and compliant motion guiding by the surgeon.

Figure 4:
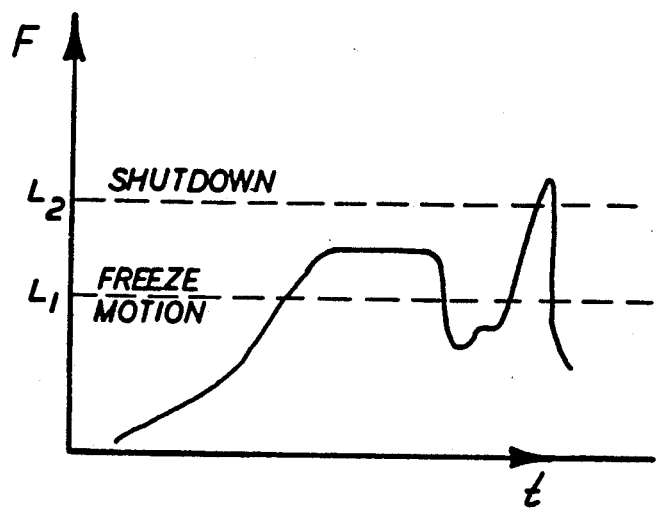
FIG. 4 is a graph of measured force, resolved at the cutter tip, as a function of time, the graph further illustrating first and second force thresholds.

The FMP 53 is interfaced to the wrist-mounted force sensor 20 and computes forces and torques resolved at the cutter 22 tip. As can be seen in the graph of FIG. 4 if any cutter 22 tip force component greater than approximately 1.5 kgf ($L_1$) is detected, the robot controller 24 is signalled to freeze motion. Forces greater than approximately 3 kgf ($L_2$) result in arm power being removed, an arm 14 "shutdown" condition. The force sensor 20 is effective in detecting such conditions as the cutter 22 stalling, encountering improperly excised soft tissue, and changes in bone hardness such as that which occurs between trabecular and cortical bone.

Also coupled to the controller 24 is a hand-held pendant 26 for use by the surgeon as an input terminal as will be described.

A motion monitoring subsystem includes, in the present embodiment, an optical tracking system having a camera 28 with three spatially separated image sensors 30a, 30b and 30c. Coupled to camera 28 is a camera processor 32 that visually tracks in three dimensions the position and orientation of a plurality of infrared (IR) beacons, such as LEDS 34, that are mounted on a reference plate 36 coupled to the robot end effector. The optical tracking system is but one of several redundant motion detecting systems employed during the cutting phase of the surgery to verify that the cutter 22 tip does not stray more than a specified amount outside of a defined implant volume. In a presently preferred embodiment of the invention the optical tracking system is a type known as Optotrak that is manufactured by Northern Digital, Inc. The three image sensors 30a-30c are line-scan devices mounted in a rigid frame which track the position of IR LEDs 34 in three dimensional space to an accuracy of 0.1 mm/m$^3$.

In the present embodiment the reference plate 36 includes eight LEDs 34 which function as positional beacons.

Camera processor 32 software is employed to compute a camera-based coordinate system from the beacon locations. Robot-to-camera and cutter-to-reference plate transformations are computed by a least squares technique from data taken with the robot arm 14 in various known positions, using appropriate linearized models.

An output 32a of the optical tracking system is coupled to a safety monitoring processor 38 that has as one function a task of verifying that the cutter 22 remains within the predetermined spatial volume associated with the selected implant. Processor 38 receives a coordinate transformation (Tcp) of the reference plate 36 relative to camera 28 from the camera processor 32. In an alternative embodiment, processor 38 receives the coordinates of LEDS 34 from camera processor 32 and computes the coordinates of reference plate 36 itself.

During a calibration phase prior to surgery, robot controller 34 moves the robot to a plurality of positions and orientations. After each motion, robot controller 24 transmits the position and orientation of the robot's cutter 22 to processor 38 over a communication bus 24a. Processor 38 uses this information, together with the reference plate 36 coordinates relative to the camera 28, to compute the coordinate transformation (Trc) between the camera coordinate system and the robot coordinate system and also to compute the coordinate transformation (Tpk) between the cutter 22 and the reference plate 36. As a result, processor 38 is enabled to determine the coordinate transformation (Trk) of the robot's cutter 22 relative to the robot from the relationship $$Trk = Trc * Tcp * Tpk. \tag{1}$$

In the presently preferred embodiment, the calibration for Tpk is accomplished by placing plate 36 in many orientations with respect to camera 28 with the tool tip being maintained in the same location. This may be accomplished either by reliance on the robot-to-tool calibration or preferably by means of a tactile search procedure using force sensor 20 to locate the cutter tip at a known constant position relative to a calibration pin or post 54. Alternative embodiments include the use of other sensing means either for direct measurement of the cutter tip position or as feedback allowing the robot controller 24 to place the cutter tip in a known position relative to a reference landmark or coordinate system.

In other embodiments of the invention the position of the manipulator arm 12 may be tracked in three dimensions by, for example, magnetic sensing devices or by an ultrasonic ranging system. That is, the practice of the invention is not limited to use with an arm motion detector that relies on detecting optical beacons.

During surgery processor 38 receives inputs over communication bus 24a from the robot controller 24 specifying, for this embodiment, a Constructive Solid Geometry (CSG) tree representation of the volume to be checked ("check volume") and the coordinates of this volume relative to the robot 12. Processor 38 repeatedly receives reference plate coordinates (Tcp) from camera processor 32 or, alternatively, receives the coordinates of LEDS 34 and computes (Tcp). Processor 38 computes Trk and determines if the cutter 22 is within the specified check volume.

Processor 38 also monitors a bone slippage detector which, in accordance with an aspect of the invention, is comprised of strain gages 40 which are physically coupled to a tissue, such as a bone 42, that is being surgically altered. The strain gages 40 are disposed to measure in three dimensions any displacement of the bone 42 relative to a bone fixator 44, the fixator 44 being rigidly coupled to the robot base 16. The strain gages 40 are interfaced through appropriate circuitry, including an analog-to-digital converter, to the processor 38.

It has been demonstrated that motions on the order of 0.1 mm are readily detectable in this manner. Furthermore, it has been determined that with a suitable fixator 44, such as a device that employs screw-type connections made directly to the bone, that even rather large forces (5 kgf) produce only a few microns of motion. Bone motion of this small magnitude is negligible in the context of this application. Thus, although no significant bone motion is expected during surgery, the strain gages 40 provide an an immediate indication if any bone slippage should occur.

If slippage of the bone is detected at least two options are available. A first option is to recalibrate the system by relocating the position of the bone in space by locating the three pins 46 with the robot effector in accordance with a procedure described below. A second option is employed if the slip sensor is accurately calibrated. The second option involves a mathematical determination of the amount of bone slippage to derive a compensation factor that is applied to subsequent robot motions. The first option is preferred for simplicity.

Further in accordance with the invention, and as illustrated in FIGS. 3a and 3b, the safety monitoring processor 38 employs a volumetric processing technique to verify that the cutter 22 tip does not stray by more than a predetermined tolerance beyond a spatial envelope that corresponds to the three dimensional implant model. The present embodiment of the invention employs the above mentioned CSG tree "check volumes", corresponding to shapes resulting from implant and cutter selection, that are constructed from primitives bounded by quadric surfaces located at a defined distance, such as one millimeter, outside of the furthest nominal excursions of the cutter 22. In FIG. 3a the volume of space that corresponds to a selected implant shape is determined by partitioning the implant shape into a plurality of primitive shapes that correspond to (a) a cutter approach volume, (b) an implant proximal portion and (c) an implant distal portion. The inner dashed line corresponds to the maximum cutter 22 excursion as measured from the center (X) of the cutter 22. The cutter 22 outer edge is thus coincident with the outer, solid envelope of the implant volume. In practice, the cutter center (X) is uniformly offset away from a longitudinal axis of the implant shape by the predetermined cutter excursion tolerance, such as one millimeter.

In accordance with CSG technique the implant primitive shapes are organized into a tree structure (FIG. 3b). A CSG tree has internal nodes that represent Boolean operations and rigid motions while the leaves of the tree represent solid primitives, here representative of the implant proximal and distal portions and the approach volume. The robot controller 24 can specify the check volumes to the safety monitoring processor 38 in at least two manners. A first approach specifies a check volume for each major phase of the surgery, such as specifying the check volume for the approach volume, then the proximal portion of the implant and subsequently specifying the check volume for the distal portion. A second approach increases the number of leaves of the CSG tree by disassociating each major portion into its constituent required cutting motions and specifying a check volume for each cut (CUT1-CUTn). A combination of these two approaches can also be used. Furthermore, each check volume may be specified immediately prior to use or may be specified at any time after the robot-to-bone transformation has been computed and stored for subsequent selection and use.

During surgery the position of the LED beacons are observed and, via the transformations discussed above, the location of the center of the cutter 22 is determined relative to the implant volume by searching and processing the CSG tree structure by known techniques. If the cutter 22 is determined to stray outside of the implant volume a command is sent by the safety monitoring processor 38 to the robot controller 24 to freeze motion. This command is preferably sent via a minimum latency path 24c, such as an optically isolated digital port. After freezing motion the robot controller 24 interrogates the safety control processor 38 via the serial communication link 24a for more detailed information regarding the "out-of-bounds" condition.

It has been determined that this technique reliably detects a motion that crosses a predetermined CSG threshold to within approximately 0.2 mm precision with constant orientation, and approximately 0.4 mm precision with cutter reorientation. Cutter motion checking rates of approximately 3-4 Hz are obtained using the present embodiment. At typical bone cutting speeds a total cutter excursion before motion is frozen is approximately two millimeters, after all system latencies are accounted for.

The surgeon-system interface further includes an online display system that includes a high resolution monitor 48 coupled to a display processor 50. The display processor 50 receives information from the robot controller 24, the safety monitoring processor 38 and a CT pre-surgery system 52. This information is combined by the display processor 50 to visually depict the progress of the cutting procedure by superimposing the CT-derived bone images and a corresponding cross-sectional view of the selected implant shape. The CT images may include both transverse and longitudinal images of the femur having appropriate cross-sectional views of the selected implant superimposed thereon. A particular cross-sectional bone image that is selected for display typically corresponds to the current depth of the cutter 22 within the femur.

The pendant 26 is a gas-sterilized hand-held data terminal that allows the surgeon to interact with the system 10 during the course of the operation. Menus invoked from the pendant 26 and displayed on the display 48 permit the surgeon to interrogate system 10 status, to select local actions such as manual guiding or withdrawal of the cutting tool, to continue a present motion, to discontinue or repeat a present step of the surgical procedure, or to restart the procedure from some earlier step altogether. One very common case is a simple "pause" function that inhibits further forward motion of the cutter 22 to allow the surgeon to satisfy himself that all is well or to permit the performance of some housekeeping function such as refilling an irrigation bottle. Pendant 26 also supports an emergency power on/off function and may also be employed to control the overall sequence of application steps and to select appropriate pre-programmed error recovery procedures should the need arise.

Each of the major system components, that is the robot controller 24, FMP 53 and safety monitoring processor 38, are enabled to freeze (inhibit) all robot motion or to turn off manipulator and cutter power in response to recognized exception conditions. If one of these conditions occurs the surgeon must explicitly re-enable motion from the hand-held pendant 26.

During surgery the principal safety monitoring requirements are (1) that the robot 12 should not "run away"; (2) that it should not exert excessive force on the patient; (3) that the cutter 22 should stay within a pre-specified positional envelope relative to the volume being cut; and (4) that the surgeon be able to intervene at any time to stop the robot 12. Once robot motion is stopped the surgeon is able, via the pendant 26, to query the robot's status, to manually guide the effector, to select an appropriate recovery procedure to continue the surgery, or to completely terminate use of the robot 12 and continue manually with the surgery.

As a part of the redundant safety monitoring of the system 10 the robot controller 24 itself routinely performs many safety and consistency checks, including such functions as determining position and velocity deadbands of the joint servos, monitoring of external signals, and the maintenance of a safety timeout monitor (STM) 24b which removes arm 14 power if the controller 24 does not affirmatively verify system integrity at predetermined intervals. In a presently preferred embodiment the interval is 16 ms. In addition to a robot power-enable relay (not shown) the controller 24 software provides facilities for disabling manipulator power, for "freezing" motion, for resuming interrupted motions, and for transferring control to predetermined recovery procedures. A number of conditions, including externally signalled consistency checks, the exceeding of force thresholds, pushbutton closures and the like interrupt the robot controller application program and cause motion to be frozen or, occasionally, arm 14 power to be removed.

In accordance with the redundant safety checking of the system 10 the combination of the arm position sensing system, including the camera processor 32, and the safety monitoring processor 38 provide an independent verification that the cutter 22 tip remains within a defined volume relative to the bone. This is accomplished by (a) verifying with the strain gages 40 that the bone does not move relative to the fixator 44, which is rigidly affixed to the robot base 14, and (b) verifying that the arm 14 end effector never strays from the defined volume in space.

The CT pre-surgery system 52 enables the surgeon to select a desired shape for the prosthetic implant 1 (FIG. 2a) and by interactively placing the implant shape upon the CT-generated images of the femur to determine where the required cavity is to be machined into the femur 2 (FIG. 2b). The pre-surgery system 52 also provides a volumetric model corresponding at least in part to the shape of the implant, the volumetric model being computer maintained and processed in order to accurately machine the implant-receiving cavity into the femoral canal. FIG. 2b illustrates the implant 1 in relation to the femur 2, the pelvis 4 and the acetabular cup 5. In a presently system 52 is implemented on an IBM PS/2-80 workstation coupled to an augmented display (PS/2 is a registered trademark of the International Business Machines Corporation).

Figure 5:
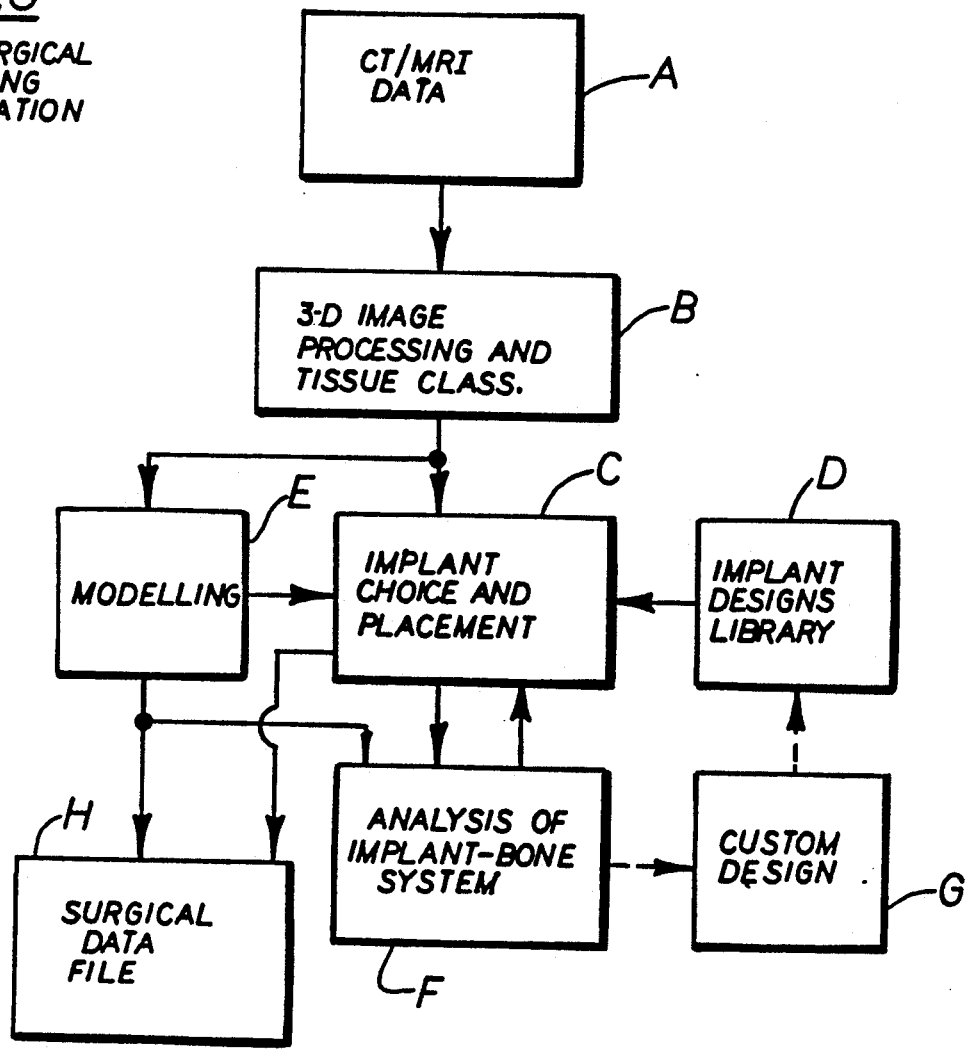
FIG. 5 illustrates information flow during pre-surgical planning.
Figure 6:
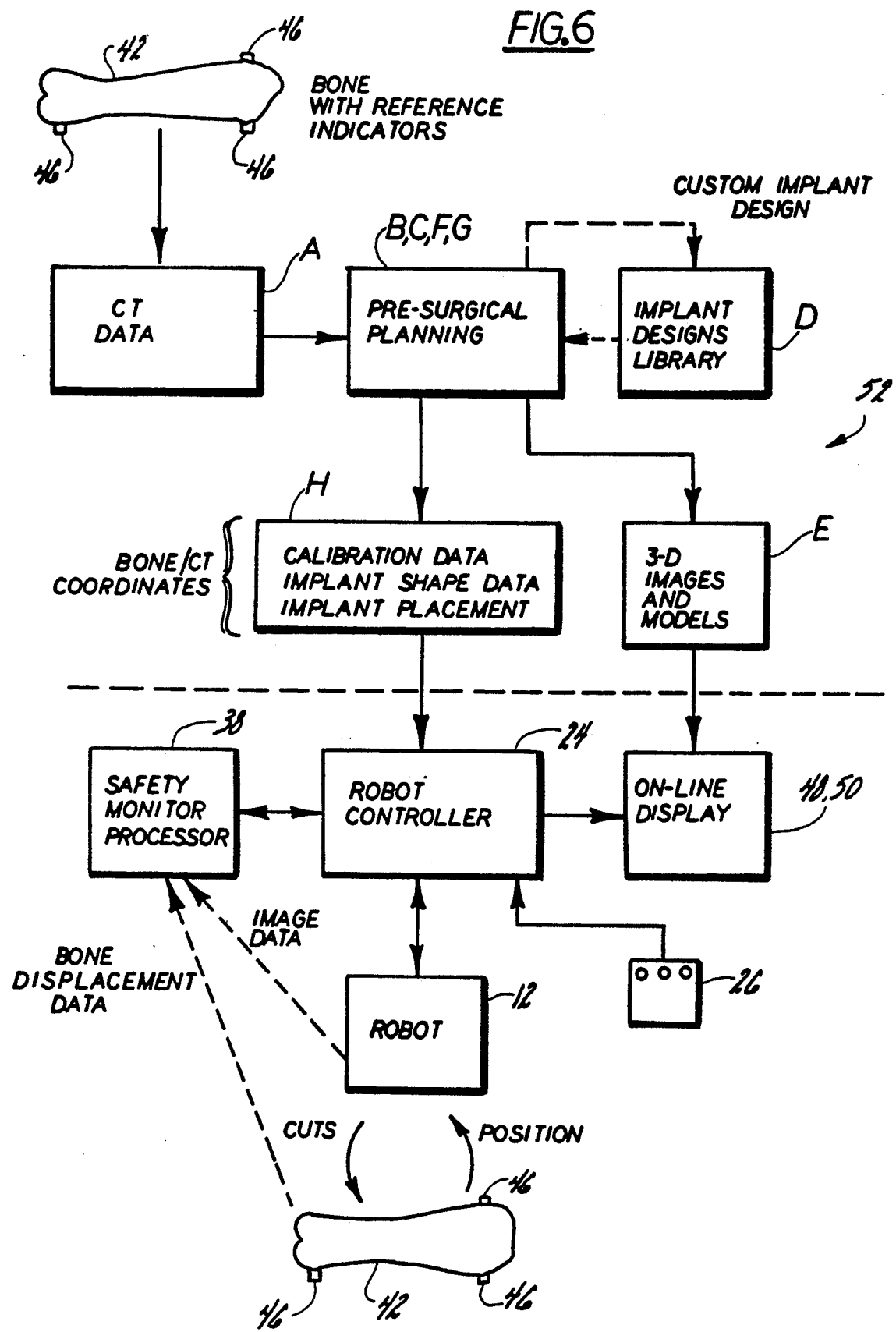
FIG. 6 is a block diagram showing in greater detail the pre-surgery system and the coupling of the pre-surgery system to the robot controller and on-line display.

Reference is now also made to FIGS. 5 and 6 wherein FIG. 5 illustrates information flow during pre-surgical planning and FIG. 6 depicts in block diagram form and in greater detail than FIG. the coupling of the pre-surgery system 2 to the robot controller 24 and on-line display processor 50. Prior to the prosthetic implant surgery the plurality of locating pins 46 are inserted into the greater trocanter and femoral condyles. A CT scan is made of the leg to generate CT data (Block A). The pre-surgery system 32 processes the CT data to produce a three dimensional CT image. The pre-surgery system 52 subsequently processes the CT image (Block B) to locate the top center of each alignment pin 46 relative to the CT coordinates, thereby determining a set of bone reference coordinates. The surgeon interactively selects appropriate orthographic cross sectional slices through the CT image of the bone. After selecting the appropriate implant shape (Block C) from an implant shape library (Block D) the surgeon interactively positions the implant model relative to the CT image as a function of bone density and other factors while the pre-surgery system 52 generates cross-sectional views and develops three dimensional models of the implant and the femur (Blocks E and F). The pre-surgical system 52 also supports an optional interactive custom design (Block G) of the prosthetic implant. This is accomplished by the surgeon entering salient structural characteristics of the femur. The resulting custom implant shape is stored within the implant designs library (Block D).

After the surgeon has placed the implant shape at a desired position within the CT image of the femur 2 the coordinates of each pin 46, together with the implant identification and the surgeon-specified implant location, are stored within a surgical data file (Block H). Three dimensional implant and bone model data generated by the modeler (Block E) is provided to the display processor 50 together with three dimensional image data from Block B. The surgical data file information is provided to the robot controller 24 so that the robot controller 24 is enabled through various "part subroutines" to determine during surgery the sequence of effector motions required to form the implant-shaped cavity at the surgeon-specified location within the femur. In an alternative embodiment the required effector motions are pre-computed relative to the pin 46 location information contained within the surgical data file. The pre-computed cutter motions are stored and may be made available, before surgery, to the safety monitoring processor 38. In either case the robot controller 24 provides the surgical data file information to the safety monitoring processor 38 for verification that the cutter 22 is operating within the spatial volume associated with the selected prosthesis shape and also for display to the surgeon so that the surgeon can monitor the progress of the cutter 22.

After the pre-surgical planning procedure described above the surgery proceeds as follows.

The patient is brought into the operating room and the surgery proceeds in a conventional manner until the point where the femoral cavity must be created. That is, the hip is opened and dislocated, the ball of the femur is cut off, and the acetabluar cup 5 is installed.

The three aligning pins 46 are exposed and the bone is placed into the fixator 44 to lock the femur firmly to the robot base 16. If used, the strain gages 40 are physically coupled to the bone.

A combination of guiding and tactile search is then employed to locate the top center of each aligning pin 46 in the robot's coordinate system. This data is used to compute the transformation between CT-based bone coordinates and robot cutter 22 coordinates.

To accomplish this pin-locating procedure a calibration ball probe is placed in the cutter 22 collet. The surgeon manually guides the robot 12 so that the ball probe tip is located approximately at the top center of one of the pins 46. This guiding may be done either from the pendant 26 or by force compliance. In force compliant guiding, the surgeon grasps any part of the robot that is distal to force sensor 20. The robot controller 24 moves the robot in response to forces detected by the force sensor 20. In the presently preferred embodiment forces and torques are resolved to a coordinate system aligned with cutter 22 and the velocity of motion is proportional to force. Alternative embodiments may employ other force compliance laws. The surgeon then manually guides the robot so that the probe tip is located a few millimeters back along the pin 46 axis. From this information, the robot controller 24 computes the estimated center and normal of the pin 46. Robot controller 24 next locates three points on the top of the pin 46 by a tactile search with the force sensor 20 and computes the exact pin normal. Finally, three points on the edge of the pin 46 are determined by tactile search and the exact pin center is located. The other two pin centers and normals are determined in a similar manner, except that previously determined pin center and normal information may be combined with measured pin positions and normals from the CT images to reduce the amount of manual guiding needed to teach approximate pin normals. The surgeon verifies the accuracy of the robot tool tip positioning before proceeding. This pin 46-related positional information is employed to compute the transformation between the CT-derived bone coordinates and the robot cutter 22 coordinates.

Next, the cutter 22 bit is placed into the collet and a further calibration check is made to verify that it is installed correctly.

The robot 12 then mills out the correct shape to receive the implant. The surgeon monitors the progress of the operation both by direct visual observation and through observation of the online display 48 where CT derived images and selected cross-sections of the implant model are superimposed.

After the shape is cut the robot is withdrawn to a standby position and manipulator power is turned off. The femoral implant 1 is installed and the femoral fixator 44 and the aligning pins 46 are removed. The operation then proceeds to completion in a conventional manner.

It should be realized that the functionality described above could be further subdivided amongst additional interconnected processors or concentrated into fewer processors. Also, although the invention has been described in the context of a hip implant application the teaching of the invention is also applicable to other surgical procedures that either do or do not require the milling of a precise shape into bone tissue. Furthermore, alternative embodiments incorporate additional measures both to reduce the robot's top speed and acceleration and to further increase the redundancy of checking. The former may be accomplished either by mechanical modifications to the manipulator arm 14 or by imposing electrical limits on motor voltage or current. The latter measure includes the incorporation of redundant position and velocity encoders monitored by a separate computer, preferably electrically isolated from the robot controller 24. If an out-of-tolerance or out-of-control condition is detected the separate computer takes appropriate action, such as asserting a manipulator "freeze" signal or by turning off manipulator power.

As such, and while the invention has been particularly shown and described with respect to presently preferred embodiments thereof, it will be understood by those skilled in the art that changes in form and details may be made therein without departing from the scope and spirit of the invention.

Having thus described our invention, what we claim as new, and desire to secure by Letters Patent is:

1. A robotic surgical system comprising:
   multiple degree of freedom of manipulator arm means including a surgical tool, the manipulator arm means being coupled to means for controllably positioning the surgical tool during the operation thereof within a three dimensional coordinate system;
   means for determining a position of the surgical tool in the three dimensional coordinate system relative to a volumetric model that corresponds at least in part to a volume of tissue to be operated on by the surgical tool, the determining means including redundant means for detecting a position of the surgical tool within the three dimensional coordinate system during the operation of the surgical tool, the detecting means having an output coupled to means for processing the volumetric model for determining the position of the surgical tool relative to the volumetric model, the processing means having an output coupled to a first input of the positioning means for causing the positioning means to suspend a motion of the surgical tool if the position of the surgical tool is detected to lie outside of the volumetric model; and means for measuring a magnitude of a force applied to the surgical tool during the operation of the surgical tool, the force measuring means having an output coupled to a second input of the positioning means for causing the positioning means to suspend a motion of the surgical tool if a force greater than a predetermined force is measured.

2. A system as set forth in claim 1 wherein the volumetric model is located within a surgical patient and wherein the system further comprises means for detecting a motion of the patient relative to the three dimensional coordinate system, the motion detecting means having an output coupled to an input of the positioning means for causing the positioning means to suspend a motion of the surgical tool if a motion of the patient is detected.

3. A system as set forth in claim 2 wherein the detecting means is comprised of strain gage means coupled between the surgical patient and a reference point within the three dimensional coordinate system.

4. A system as set forth in claim 3 wherein the system includes means for immobilizing a portion of the patient that includes the volumetric model, and wherein the reference point is located upon the immobilizing means.

5. A system as set forth in claim 1 wherein the measuring means includes means for resolving at a tip of the surgical tool an applied force and torque.

6. A system as set forth in claim 1 and further comprising means having an input coupled to an output of the position determining means and, responsive to a calibration procedure that positions the surgical tool at at least one predetermined location within the three dimensional coordinate system, for determining a coordinate transformation for locating the volumetric model within the three dimensional coordinate system.

7. A system as set forth in claim 1 wherein the volumetric model corresponds to a three dimensional shape of a prosthetic implant, the volumetric model additionally corresponding to a surgical tool approach volume relative to the prosthetic implant, and wherein the processing means determines the position of the surgical tool relative to both the three dimensional shape of the prosthetic implant and to the surgical tool approach volume.

8. A system as set forth in claim 1 wherein the surgical tool is a cylindrical rotatable cutter.

9. A system as set forth in claim 1 wherein the processing means processes the volumetric model as a constructive solid geometry (CSG) tree data structure representation thereof.

10. A system as set forth in claim 1 wherein the detecting means is comprised of imaging means disposed for imaging a region of space that includes at least a portion of the manipulator arm means.

11. A system as set forth in claim 10 wherein the volumetric model is represented as a constructive solid geometry (CSG) tree data structure, and wherein the imaging means has an output coupled to the volumetric model processing means, the volumetric model processing means including means, responsive to an image indicating a location of the manipulator arm means, for processing the CSG tree data structure for determining if the surgical tool is positioned within the volumetric model.

12. A system as set forth in claim 1 and further comprising means, coupled to the force measuring means, for determining through a force compliance technique a location of at least one reference point within the three dimensional coordinate system.

13. A system as set forth in claim 1 and further comprising means, responsive to an output of the position determining means, for displaying to an operator of the system a position of the surgical tool relative to the volumetric model, the displaying means including means for superimposing computed tomagraphy (CT) information with corresponding cross-sectional images of the volumetric model.

14. A system as set forth in claim 1 and further comprising means, coupled to the force measuring means, for halting a further motion of the surgical tool if a force exceeding a first threshold is measured and for uncoupling the manipulator arm means from a source of power if a force exceeding a second, threshold is measured.

15. An apparatus for preparing a cavity within a bone to receive a prosthetic implant, comprising:

multiple degree of freedom manipulator arm means including a rotating surgical tool, the manipulator arm means being coupled to means for controllably positioning the surgical tool within a three dimensional robot coordinate system;

means for immobilizing the bone within the three dimensional robot coordinate system;

means for determining a position of the surgical tool in the three dimensional robot coordinate system relative to a volumetric model representative of a cavity to be formed within the bone, the determining means including imaging means disposed for imaging a region of space that includes at least a portion of the manipulator arm means for determining if the surgical tool is positioned outside of the volumetric model, the determining means having an output coupled to a first input of the positioning means for causing the positioning means to suspend a movement of the surgical tool if the position of the surgical tool is determined to lie outside of the volumetric mode; and means coupled between the bone and the immobilizing means and having an output for indicating an amount of movement, if any, between the bone and the immobilizing means, the indicating means measuring the movement of the bone in three dimensions, the movement indicating means having an output coupled to a second input of the positioning means for causing the positioning means to suspend a movement of the surgical tool if a movement of the bone is indicated.

16. An apparatus as set forth in claim 15 wherein the volumetric model is represented as a constructive solid geometry (CSG) tree data structure, and wherein the determining means includes means for processing the CSG tree data structure for determining if the surgical tool is positioned outside of the volumetric model and for suspending a further movement of the surgical tool if the surgical tool is determined to be positioned outside of the volumetric model.

17. An apparatus as set forth in claim 15 and further comprising means for measuring a magnitude of a force applied to the surgical tool, the force measuring means having an output coupled to the means for controllably positioning the manipulator arm means for causing the positioning means to suspend a movement of the surgical tool if the force is found to exceed a predetermined magnitude.

18. An apparatus as set forth in claim 15 wherein the movement indicating means is comprised of strain gage means.

19. An apparatus as set forth in claim 15 wherein the bone has a plurality of reference pins affixed thereto for defining points of a bone coordinate system, and wherein the apparatus further comprises means, responsive to an operator manually guiding a tool to at least a first one of the reference pins, for determining a transformation between the bone coordinate system and the three dimensional robot coordinate system, the transformation determining means having an input coupled to an output of the imaging means.

20. An apparatus as set forth in claim 19 wherein the transformation determining means further includes means, responsive to an image indicating a location of the manipulator arm means, for determining a transformation between the three dimensional robot coordinate system and a three dimension coordinate system associated with the imaging means.

21. An apparatus for preparing a cavity within a bone to receive a prosthetic implant, comprising:

multiple degree of freedom manipulator arm means controllably conveying a surgical tool so as to remove bone tissue therewith, the manipulator arm means being coupled to means for controllably positioning the surgical tool within a three dimensional robot coordinate system;

means for determining a position of the surgical tool in the three dimensional robot coordinate system relative to a volumetric model representative of a three dimensional shape of a cavity to be formed within a bone, the determining means including imaging means disposed for obtaining a three dimensional image of at least a portion of the manipulator arm means for determining if the surgical tool is positioned outside of the volumetric model, the determining means having an output coupled to a first input of the positioning means for causing the positioning means to suspend a movement of the surgical tool if the position of the surgical tool is determined to lie outside of the volumetric model; and means for measuring a magnitude of a force applied to the surgical tool while removing bone tissue during the preparation of the cavity, the force measuring means having an output coupled to a second input of the positioning means for causing the positioning means to suspend a motion of the surgical tool if a force greater than a predetermined force is measured.

22. An apparatus as set forth in claim 21 and further comprising:

means for immobilizing the bone; and strain gage means coupled between the bone and the immobilizing means and having an output for indicating an amount of movement, if any, between the bone and the immobilizing means, the strain gage means indicating a movement of the bone in three dimensions and having an output coupled to a third input of the positioning means for causing the positioning means to suspend a motion of the surgical tool if a movement of the bone is indicated.

23. An apparatus as set forth in claim 21 wherein the bone has a plurality of reference pins affixed thereto for defining points within a bone coordinate system, and wherein the apparatus further comprises means, responsive to an operator positioning the manipulator arm means so as to contact a point on one of the reference pins, for autonomously repositioning the manipulator arm means for determining, in conjunction with the force measuring means, a center of the reference pin and a normal to the reference pin.

* * * * *